(12) United States Patent
Eidson

(10) Patent No.: US 8,852,562 B2
(45) Date of Patent: Oct. 7, 2014

(54) ARTIFICIAL TANNING SOLUTION AND OTHER FLUID APPLICATION APPARATUS, SYSTEM AND METHOD

(76) Inventor: Richard H. Eidson, Fairfield, IA (US)

( * ) Notice: Subject to any disclaimer, the term of this patent is extended or adjusted under 35 U.S.C. 154(b) by 1248 days.

(21) Appl. No.: 10/924,305

(22) Filed: Aug. 23, 2004

(65) Prior Publication Data

US 2006/0037532 A1     Feb. 23, 2006

(51) Int. Cl.
- *A61K 8/00* (2006.01)
- *A61K 8/18* (2006.01)
- *A61Q 17/04* (2006.01)
- *A61K 8/02* (2006.01)
- *A61Q 19/04* (2006.01)

(52) U.S. Cl.
CPC . *A61Q 19/04* (2013.01); *A61K 8/02* (2013.01); *A45D 2200/057* (2013.01)
USPC .............................. 424/59; 424/400; 424/401

(58) Field of Classification Search
USPC ........................................... 424/59, 400, 401
See application file for complete search history.

(56) References Cited

U.S. PATENT DOCUMENTS

| | | | |
|---|---|---|---|
| 4,034,900 A * | 7/1977 | Hafele | 222/321.9 |
| 5,277,341 A * | 1/1994 | Privas | 222/333 |
| 5,425,753 A | 6/1995 | Wege | |
| 5,922,333 A | 7/1999 | Laughlin | |
| 6,298,862 B1 | 10/2001 | Laughlin | |
| 6,416,747 B1 | 7/2002 | Laughlin | |
| 6,546,570 B1 | 4/2003 | Eidson | |
| 6,799,090 B2 * | 9/2004 | Farina et al. | 700/283 |

\* cited by examiner

*Primary Examiner* — Abigail Fisher
*Assistant Examiner* — Luke Karpinski
(74) *Attorney, Agent, or Firm* — McKee, Voorhees & Sease, P.L.C.

(57) ABSTRACT

An apparatus, method, composition, and system for coating of the skin of a person with a fluid. In one aspect, the apparatus includes a relatively small, lightweight framework that supports a reservoir for containing a tanning solution, a plurality of misting heads for simultaneously dispensing relatively short, gentle misting bursts of the tanning solution upon operation of actuators.

21 Claims, 8 Drawing Sheets

ARTIFICIAL TANNING SOLUTION AND OTHER FLUID APPLICATION APPARATUS, SYSTEM AND METHOD

I. BACKGROUND OF THE INVENTION

A. Field of the Invention

The present invention relates to an artificial tanning composition, and an apparatus, system and method of use for applying fluids to a person's body. In particular, the present invention relates to an economical, effective composition, apparatus, system, and method for applying a substance to human skin.

B. Problems in the Art

Many people desire to have noticeably tanned skin. This is conventionally achieved by exposing the skin to ultraviolet ("UV") light from the sun or generated in tanning booths or beds. Either method requires a lot of time, particularly if the tan is to be maintained over a substantial length of time. Tanning booths or beds can also be expensive to buy or use.

In the last several decades, the medical community has become increasingly vocal about the health risks associated with UV skin tanning. More recently, there have been explicit warnings to avoid prolonged exposure to UV on the skin, whether via sunlight or tanning booths or beds, because of such risks.

Avoiding sunlight or tanning booths is one solution but, of course, forfeits any substantial tan. Another approach is to block UV from the skin. A large variety of "sun blocks" has been and is available commercially. However, such blocks usually prevent light from reaching the skin and, thus, also do not allow that area of the skin to easily tan.

There has been increasing demand for an alternative to UV tanning that provides at least the appearance of tanning. One such alternative is use of substances that color the skin, with the goal of simulating a tan or producing what will be called an artificial tan. Certain substances, when applied to the skin, produce the appearance of darkened or tanned skin. For example, for some time it has been known that dihydroxyacetone ("DHA"), basically a simple sugar, produces a darker appearing skin when applied. There have been a variety of commercial or home-made artificial tan solutions that include DHA. Some are in liquid form. Others are in lotion form.

The conventional method of application of a DHA solution is by wiping or rubbing it on the skin by hand with a towel or cloth; by what will be called the "manual" application method. The user has substantial control on where the substance is applied. However, it is difficult for the user to apply it evenly, or at all, to certain parts of his/her own body. A complete application usually requires another person. Even so, it is difficult to get the right amount on for a natural, even looking artificial tan. In any event, it takes up substantial time and effort to apply.

Also, manual application can produce spills or over-application. For example, such substances would color any skin. If exposed to one's palms, inside forearms, or other body parts, it may not look like a natural tan. Furthermore, over-application on body parts can produce unnatural looking coloring or color variation. Over-application can also make it easier for the substance to rub-off or stain clothing on the user or others, or rub-off or stain furniture. Spills can require burdensome clean up or cause damage to floors, furniture, or clothing.

While artificial tanning substances do not carry the health risks associated with UV-achieved tans, manual application of such substances has certain deficiencies, as indicated above. Some attempts to improve application of artificial tanning substances have been made. For example, some artificial tanning solutions are directed to be applied with hand-operated spray bottles. While this tries to avoid deficiencies of manual application, it still suffers from issues similar to those of manual application. It is still difficult for the user to reach all desired body parts. It can result in over-application, overspray, or spills. It can result in exposure of the solution to eyes or mouth. It is substantially dependent on the skill of the person applying the solution.

Thus, there have been attempts at systems which automatically or semi-automatically apply artificial tanning solutions to the body. Such systems disclose methods and apparatus to attempt to apply artificial tanning solution without the uncertainties and burdens of manual application or of spray bottles. For example, U.S. Pat. No. 5,922,333 to Laughlin discloses a method of coating human skin with a skin coating composition by utilizing a machine to spray a liquid composition in a continuous pattern under substantial pressure onto the body, and capturing and recirculating the spray not deposited on the body. Described methods of atomizing include pneumatic, electrostatic, ultrasonic, and airless atomization.

U.S. Pat. No. 6,298,862 to Laughlin discloses much the same information as U.S. Pat. No. 5,922,333 but the claims are directed to an apparatus rather than a method. A booth or enclosure is disclosed to position the user and to contain the artificial tanning solution. It is substantially larger than most humans. It therefore takes up a substantial space. It can occupy a substantial foot-print of floor space, which is many times precious for businesses. They also can take significant time and resources to set up. They are not portable. They can be complicated to operate, requiring a trained person to run the system.

U.S. Pat. No. 6,416,747 to Laughlin is related to U.S. Pat. No. 5,922,333 and U.S. Pat. No. 6,298,862 but the claims are directed to a plural component process for coating the human body where first and second components, incompatible premix, are mixed simultaneously with application.

The compositions disclosed in the Laughlin patents include not only DHA in solution, but a variety of other substances. Some of these other substances are used to deter running or dripping of the solution. However, some such substances pose health risks to humans if inhaled or if exposed to mucus membranes, eyes or lips. And, while the U.S. Food and Drug Administration ("FDA") has approved DHA for external use on humans, it has warned of safety issues if DHA is exposed internally to humans, to lips, the eyes or surrounding areas, or to any body surface covered by mucous membrane. The FDA warns it is difficult to avoid exposure in a non-approved manner with conventional spray booths. Relatively high pressure continuous sprays in an enclosed booth make it difficult to avoid inhalation or exposure to such body surfaces and areas.

Also, pressurized sprays and an enclosed booth can be susceptible to over-application, especially in areas directly in line with spray heads or nozzles. Some existing spray booths spray at about 300 psi. They tend to use a substantial amount of solution to try to reach and cover most external body parts. Such application methods require towel buffing to even out the solution on the skin or remove excess. Thus, this adds back in manual application steps to the process, which adds time and burden, and which is inconsistent with trying to make application automatic. Existing spray booths tend to be relatively expensive; some costing in the neighborhood of thirty or forty thousand dollars.

Therefore, there is room for improvement in the art.

II. SUMMARY OF THE INVENTION

A primary object, feature, aspect, or advantage of the present invention is a composition, apparatus, system and method which improves over or solves problems and deficiencies in the art. There is a need for an automatic or semi-automatic system that is economical, is easy to assemble and operate, uses an effective, simple, safer tanning solution, and provides a quick, natural-looking artificial tan.

Further objects, features, aspects, and advantages of the present invention include one or more of, but are not limited to, a composition, apparatus, system or method which:
  a. does not require containment of the misted solution or enclosure of the person being artificially tanned.
  b. does not require recirculation of overspray.
  c. avoids continuous, relatively high pressure spray for application.
  d. does not require a separate operator.
  e. is relatively compact and light weight, and in some forms, can be portable.
  f. can be used indoors, and many times, outdoors.
  g. is relatively non-complex.
  h. is economical to make, operate, and maintain.
  i. promotes a natural looking artificial tan.
  j. deters running or unevenness of the tanning solution.
  k. deters the need for buffing or wiping or other steps to apply evenly.
  l. deters exposure to undesirable body parts or inhalation.
  m. can use a tanning solution that has less health risks and is simpler in composition.
  n. is economical to manufacture, durable in use, and efficient in operation.

These and other objects, features, aspects and advantages of the present invention will become more apparent with reference to the accompanying specification and claims.

The present invention is an artificial tanning composition, apparatus, system and method for coating the skin of a person with artificial tanning solution. In one aspect of the invention, an apparatus includes a framework that supports an array of misting heads, a reservoir for containing an artificial tanning solution, and actuators that cause the misting heads to release periodic, gentle bursts of artificial tanning solution. The bursts expand and fall by gravity onto the person's skin. Enclosure, containment, or recirculation of the misted tanning solution is not required because the solution falls by gravity gently on the skin, tends to adhere, and the solvent (usually water) almost simultaneously evaporates. This promotes an even, natural-looking artificial tan and deters color variation, over-spray, over-application, or the need to capture excess. It also tends to deter any need for manual methods to complete the process.

Another aspect of the invention includes a method of artificial tanning comprising generating intermittent, misted bursts of artificial tanning solution which expand and drop by gravity onto a user's skin. Optionally, the user drys off between sets of bursts and rotating the body between sprays to expose uncoated skin.

Another aspect of the invention is an artificial tanning solution that essentially consists of DHA and water. This eliminates additives that many others utilize, some of which can pose health issues.

Another aspect of the invention is a kit consisting essentially of a DHA/water solution in a bulk container, a framework supporting a plurality of misting heads, a fluid conduit from the bulk container to each misting head, and an actuator that can operate the misting heads to produce intermittent bursts of mist of the tanning solution.

There are several advantages to aspects of the present invention. It can be automated to the point that the person receiving the artificial tan can by him/herself start and complete the application of the tanning solution without the need for other persons. The application of tanning solution is even due to the misted bursts of tanning solution Drying is quicker than that with other systems because of the minimal amount and the manner of delivery. In addition, the fine mist created by the present invention disperses the spray well. Finally, the components of the artificial tanning solution are simple and safer; dihydroxyacetone and water.

III. BRIEF DESCRIPTION OF THE DRAWINGS

FIG. 1 is a perspective view of a recumbent artificial tanning system according to one exemplary embodiment of the present invention.

FIGS. 2A-C are enlarged, isolated front elevation views of actuators and misting heads of the embodiment of FIG. 1.

IV. DETAILED DESCRIPTION OF EXEMPLARY EMBODIMENTS

A. Overview

Figure 1:
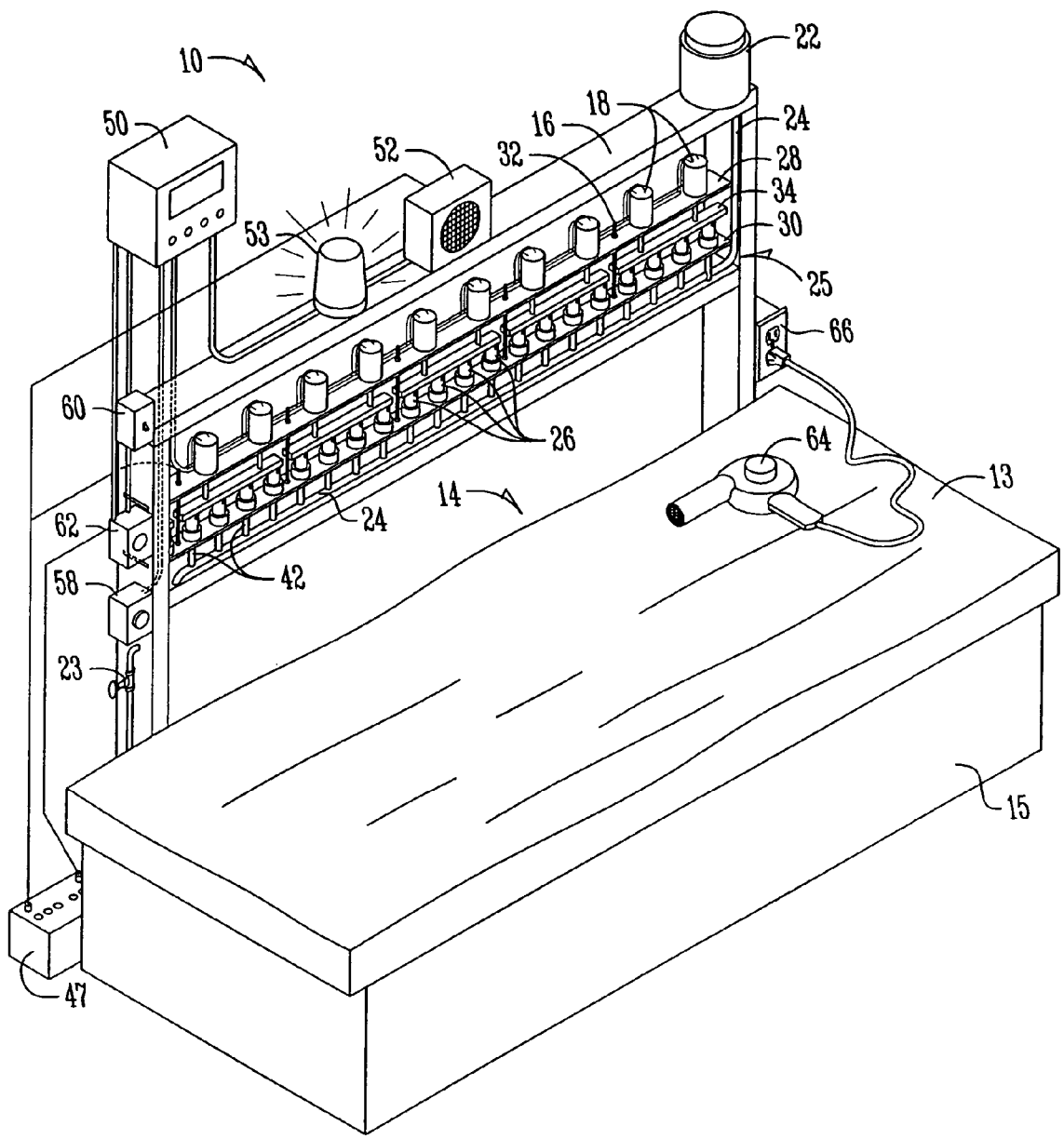

To assist in an understanding of the present invention, examples of a few forms it can take will now be described in detail. It is not intended that the present invention be limited to the described embodiments, which are provided by example only and not by way of limitation. It is intended that the invention cover all modifications and alternatives which may be included within the spirit and scope of the invention.

Frequent reference will be made to the accompanying Figures. Reference numerals or letters are used to indicate certain parts or locations in the Figures. The same reference numerals or letters will be used to indicate the same parts or locations unless otherwise indicated.

B. General Apparatus

By reference to FIG. 1, an artificial tanning system 10 is illustrated in one exemplary embodiment. The basic components of system 10 comprise a reservoir or container 22 of artificial tanning solution, a sub-system to move solution out of container 22 and gently mist the solution in bursts, and a framework to support such components in an arrangement that distributes the bursts of mist to selected body parts of a user.

As indicated in FIG. 1, for a recumbent system 10, the framework can include a bed 14 and an adjacent support 16. The misting sub-system here comprises a plurality of misting heads 26 spaced apart along bed 14 on support 16. Misting heads 26 are in fluid communication with reservoir 22 by suitable tubing. Misting heads 16 shown here are essentially commercially available spring-loaded, push down spray heads like are used in a wide variety of spray bottles. Downward movement of the head 26 causes movement of artificial tanning solution through the tubing and out an orifice in a mist-type form. Electrically powered actuators 18 intermittently simultaneously depress misting heads 26 and allow spring-return of the heads 26. This produces intermittent relatively short bursts of gentle mist from heads 26 all along bed 14.

One or more bursts can be generated for each side of the user (front, back, left side, right side). The user can simply rotate on bed 14 between bursts or sets of bursts for complete coverage of the user's body. The misted bursts expand from heads 26 and gently fall by gravity towards bed 14. Because of this action, the water solvent of the solution begins immediately to evaporate, promotes even coverage and deters running of the solution on the body. It also eliminates the need for an enclosure around the user to contain spray at relatively high pressure, or the need to capture excess that does not adhere to the user's body.

Therefore, unlike spray booths that completely enclose the user and subject the user to confined close space to contain the relatively high pressure spray and capture excess, system 10 can be open, can be lightweight and even portable, and can use relatively non-complex components and compositions in a manner that is less likely to result in safety issues for users.

Figure 3:
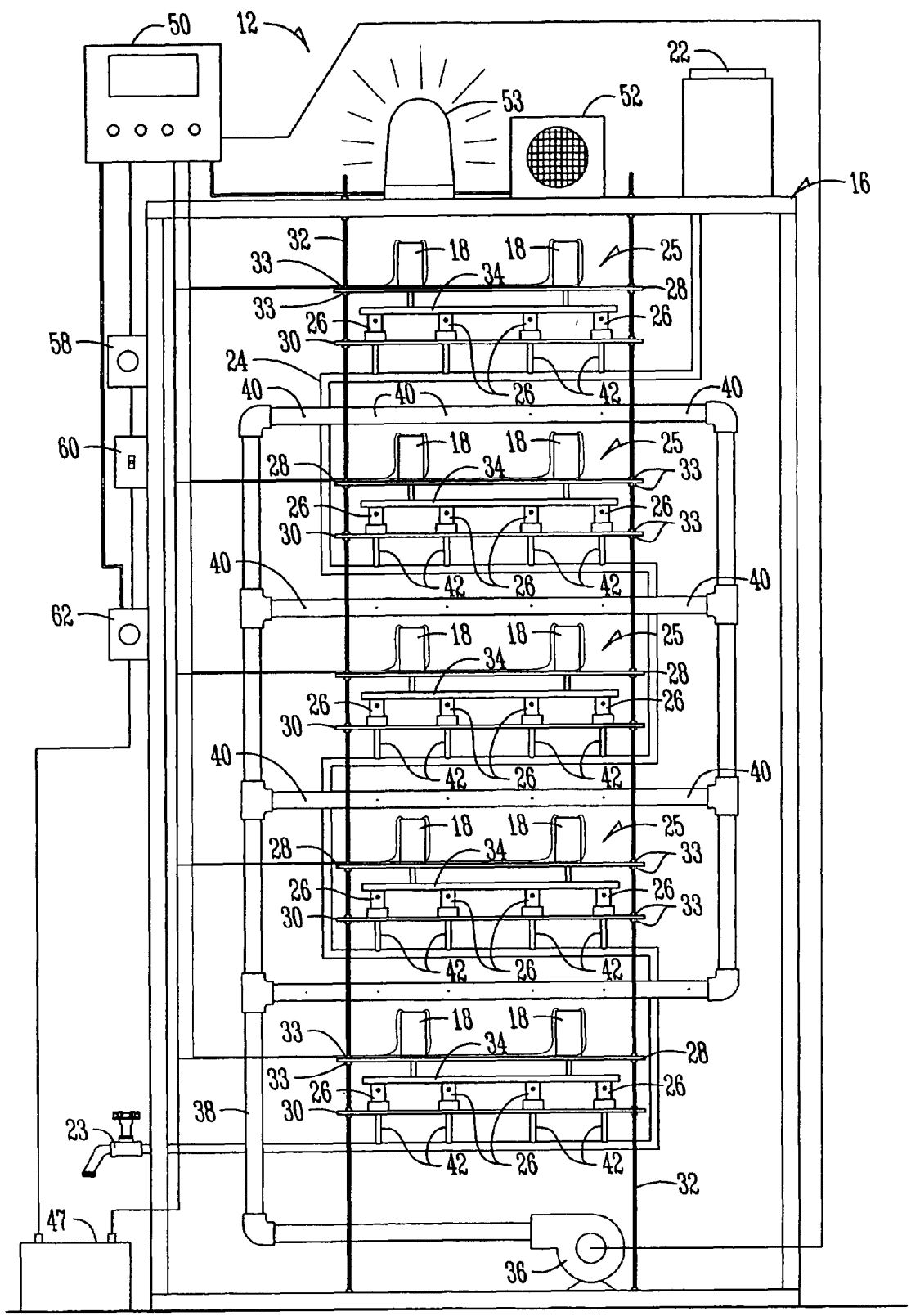
FIG. 3 is a front elevation view of an upright artificial tanning system according to another exemplary embodiment of the present invention.

The system can take different forms and embodiments. For example, FIG. 3 shows an upright system 12. Like system 10, it has a framework support for a plurality of misting heads 26, a reservoir 22, conduit between reservoir 22 and heads 26, and actuators 18 to operated heads 26. However, it does not require a bed 14. The user stands adjacent heads 26, which match up roughly with a user. Such a system 12 is relatively narrow, lightweight, inexpensive, and takes minimal floor space.

C. General Composition of Artificial Tanning Solution

One aspect of the invention is an artificial tanning solution that is an improvement over those conventionally used in present artificial tanning spray booths. As previously mentioned, many conventional solutions that include DHA also include one or more additional substances in addition to DHA and water. This is believed necessitated to try to deter running of the solution. These other substances can include, for example, emulsifiers or other chemicals to try to make the pressurized spray adhere to skin.

One embodiment of artificial tanning solution according to the present invention is solution consisting essentially of DHA and water. The solvent is simply water and the solute is dihydroxyacetone (DHA), widely used in commercial artificial tanning products and recognized as safe and effective, for certain purposes, by the FDA.

The preferred concentration of DHA in the solvent is from 2% to 20%. More preferably, the concentration of DHA in the solvent is from 5% to 15%.

One method of preparation of the tanning solution is to dissolve 85 grams of dihydroxyacetone (colorless, crystalline solid) in 500 ml of water. More water is added until the solution reaches 1 liter. This produces an 8.5% solution in the water.

This solution has been found effective for a natural-looking artificial tan when applied by gentle misting bursts that are allowed to fall by gravity onto a user's skin.

D. Specific Exemplary Embodiment One

Construction and use of the exemplary embodiment of FIG. 1 will now be described in even more detail FIG. 1 depicts in general perspective view a recumbent artificial finning system 10. Bed 14 is constructed such that a person (the client) receiving that application of tanning solution is able to lie fully extended upon the bed's surface. Bed frame 15 is constructed with materials with sufficient strength and rigidity to hold the possible range of human body weights. FIG. 1 depicts the bed with an optional mattress pad 13 used for the comfort of the client. The surface of the bed is below the level of the misting heads 26 and is generally parallel to the plane of the floor upon which it is supported.

FIG. 1 shows the recumbent artificial tanning system with a frame 16 to support the misting heads 26, actuators 18, and associated components. Frame 16 is shown constructed of lumber (e.g. 2×4s), which is relatively inexpensive, strong, and easy to shape and connect. The lumber could be replaced with any material of sufficient strength and rigidity to support the components mounted to it. The pieces of frame 16 can be secured together by nails, screws, bolts, and/or joints.

Two metal mounting plates 28, 30 (e.g. 2"×6' aluminum flat bars) are mounted to the frame 16 such that the flat surfaces of the mounting plates are generally parallel to the bed's surface as depicted in FIG. 1. The mounting plates 28, 30 are inserted into generally horizontal slots formed in the vertical pieces of frame 16. Other methods of mounting are possible.

Figure 2A:
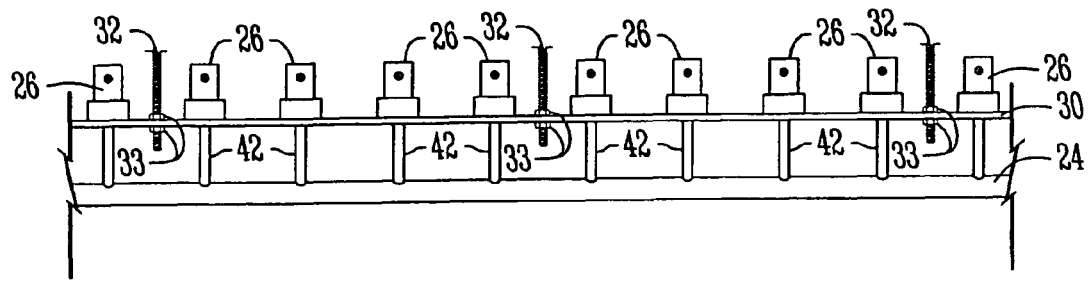
Figure 2B:
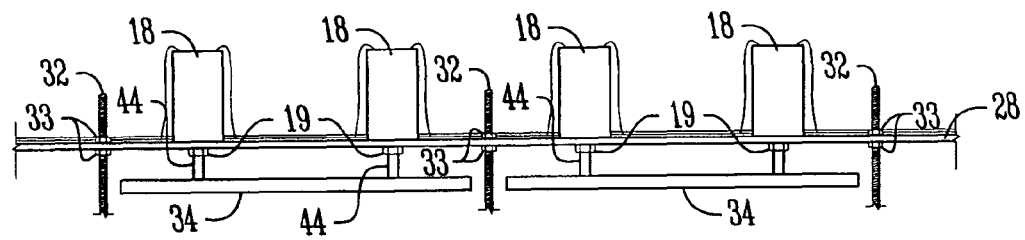
Figure 2C:
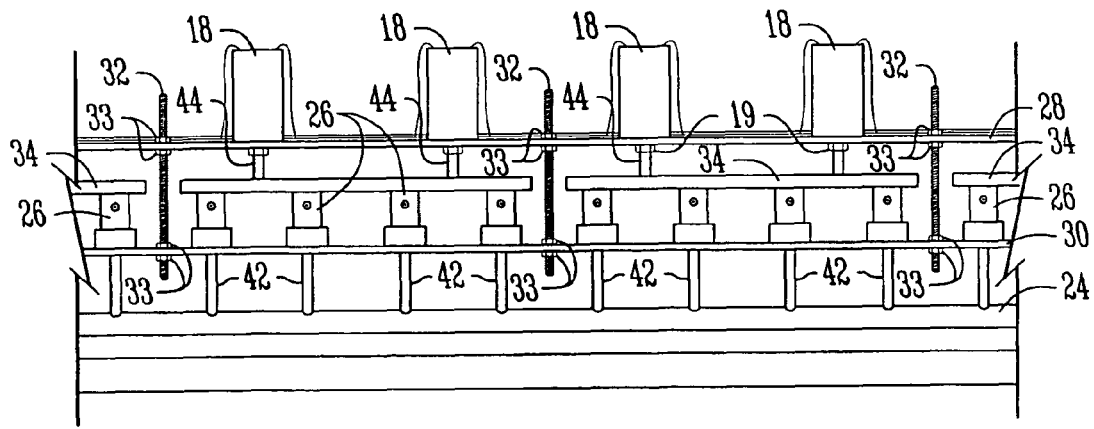

FIGS. 2A-C are enlarged views of the misting head assembly 25, or parts thereof. Threaded steel rods 32 are used to maintain the spacing between mounting plates 28, 30 along their lengths. The threaded steel rods 32 are placed through aligned holes drilled through mounting plates 28, 30. The threaded steel rod 32 and the mounting plates 28, 30 are held in rigid relationship through the use of nuts 33 tightened against each side of the mounting plates 28, 30 along the threaded rod 32.

The misting head assembly 25 consists of two main subsystems.

FIG. 2A shows, in isolation, a first subsystem, misting heads 26. Each misting head 26 comprises a pump action emitter and a feeder tube 42. A commercially available misting head 26 is United States Plastic Corp. number 180614 polypropylene covered finger sprayer. The pump-action misting head 26 is attached to the upper surface of lower mounting plate 30. Misting heads 26 are held in place via a surface adhesive and the attachment of a feeding tube 42 running through an aperture in lower mounting plate 30. In turn, each feeding tube 42 is connected in fluid communication to a vinyl tube 24 carrying artificial tanning solution from reservoir 22. The outlet orifice of each misting head 26 is positioned to dispense solution generally normal to the plane of frame 16.

The second subsystem is shown in isolation in FIG. 2B. Sets of linear solenoid actuators 18 and press bars 34 are mounted on upper mounting plate 28. Each solenoid has a linearly moveable arm 44 that extends below plate 28 along a longitudinal axis. The press bar here comprises a wood piece (e.g. 1"×1") interference fit into a u-shape metal channel. The distal end of arm 44 is fixedly attached to the wood piece (e.g. interference fit) of press bar 34 in such a manner that press bar 34 moves with arms 44 and can overcome the spring force of misting heads 26.

In the example of FIGS. 1 and 2A-C, there are two solenoids per press bar 34. In a normal position, arms 44 of solenoids 18 are retracted along the longitudinal axis into their respective solenoid bodies. Upon actuation of solenoids 18, arms 44 move outwardly along the longitudinal axis. This pushes bars 34 downwardly.

One examples of commercially available linear solenoid actuator 18 is a McMaster-Carr Model 69905k79. The lower end of the body of the solenoid 18 has a threaded male portion. An aperture in upper mounting plate 28 is sized to accept the threaded male portion. A nut 19 is tightened onto the threaded male portion from below plate 28 to fix solenoid 18 to plate 28. The arm or rod portion 44 of solenoid 18 extends through the male threaded portion. The preferred solenoid has a maximum stroke of 1" and exerts 130 oz. of force over a ⅛" stroke. The retracted rod 44 length is 2.04" and the diameter of the rod is 0.187". The mounting threads are 1" in diameter so the holes through the upper mounting plate 28 should be slightly larger to facilitate mounting the solenoid actuators 18. The use of the McMaster-Carr 69950k79 should not be seen to limit the use of other technology that creates a force to push down misting heads 26.

The stroke and force of solenoids 18 is controlled such that a burst from misting head 26 could last approximately $\frac{2}{3}^{rd}$ of a second and issue at no more than approximately 30 psi. This is relatively low pressure. It creates a controlled, gently burst of mist for a limited period of time. It basically comes out, expands a bit, and then falls by gravity. Importantly, it is generally a fixed and limited quantity that is dispensed per burst, not a continuous spray. Other burst periods and psi's are, of course, possible.

Each press down bar 34 is attached to two solenoid rods 44 such that each solenoid 18 exerts a similar amount of force along the length of the press down bar 34. The press down bar 34 will be of sufficient length that when mounted in the misting head assembly 25 it is in contact with four misting heads 26.

FIG. 2C illustrates the two subsystems in normal position. FIG. 2C shows that when the press down bar 34 is properly aligned and adjusted in the misting head assembly 25, in its normal position it will abut or be closely adjacent the top of its respective misting heads 26. Mist heads 26 have a spring which holds them in an upward extended normal position.

By referring again to FIG. 1, the artificial tanning solution is carried to the feed tubes 42 in a vinyl tube 24 with a 9/16" outer diameter and a ⅜" inner diameter. The vinyl tube 24 leads from reservoir 22 containing the artificial tanning solution which is mounted on the top of the frame 16. Reservoir 22 holds in excess of one liter of the artificial tanning solution. Gravity is used to carry the artificial tanning solution into vinyl tube 24 and into the feed tubes 42, which are in fluid communication with tube 24. The distal end of tube 24 here is directed through the left-hand vertical frame member and downward. A valve 23 is installed upstream of the distal end of vinyl tube 24, as depicted in FIG. 1, to normally close that end of tube 24 but facilitate draining the artificial tanning solution and air from the fluid circuit of the artificial tanning system 10 when desired.

In this example, solenoids 18 would be wired to simultaneously move all press arms 34, in a controlled manner, to in turn simultaneously push down all misting heads 26 for a moment. This produces a controlled, gently "burst" of mist from each misting head 26. Cumulatively the gentle mist bursts would expand but fall by gravity. System 10 would be adjusted such that the mist bursts would fall over approximately the area of bed 14 in as uniform manner as possible, without much, if any, falling outside that area. Such adjustments are possible by selecting the stroke, speed, and force of solenoids 18, and the type of misting head 26. As can further be appreciated, the positioning of misting heads 26 is above a user's body when lying on bed 14, and the direction of their outlet orifice causes the misting bursts or clouds to travel first outwardly, but then, by gravity, fall onto the user.

Figure 4:
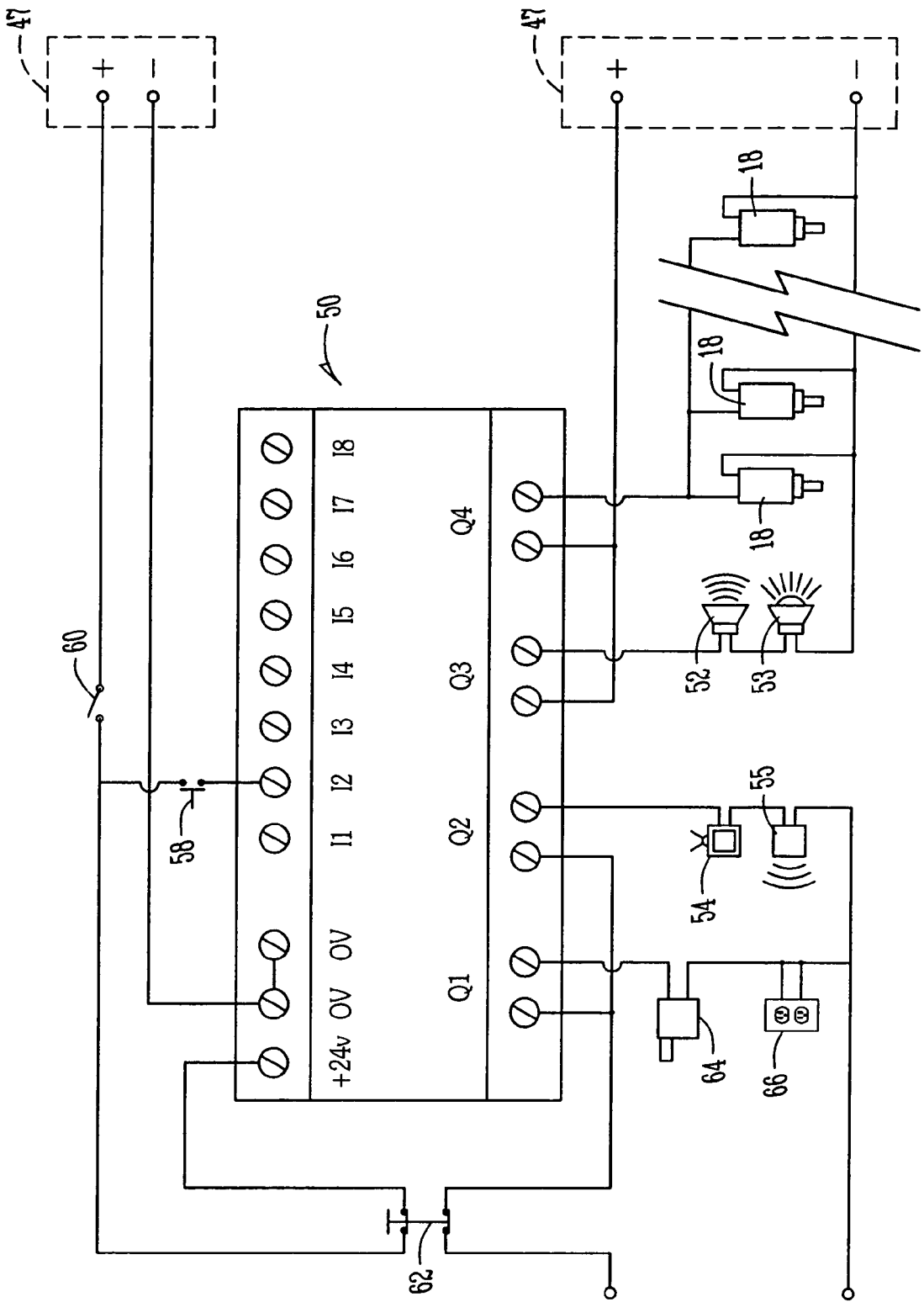
FIG. 4 is a schematic diagram of one exemplary electrical circuit for use with either system of FIG. 1 or 3.

There are a variety of possible ways to control operation of system 10. One simple way would be to wire all solenoids 18 in parallel to an electrical power source, and have a user operable single switch (e.g. a simple hand or foot switch within reach of the user when lying on bed 14) which causes a single controlled simultaneously burst from each misting head. The user could decide how many bursts per body side and their timing. FIG. 4 illustrates such a circuit. It should be noted that system 10 could be powered by a battery source. This enhances portability of system 10 as well as allows operation away from a conventional AC household or commercial outlet (e.g. would allow use outdoors on a beach).

Wiring for the actuation of the solenoids 18 should be such that the wires are attached to the frame 16 and the upper mounting plate 28 in a way that the moving solenoid rods 44 and press bar 34 do not pinch nor pull upon the wires.

An alternative, diagrammatically illustrated at FIGS. 1 and 4, would be to control actuators 18 by a programmable logic controller (PLC) 50. An example of a PLC would be the Klockner Moeller Easy412-DC-R mini PLC. In this embodiment, two 12 volt batteries 46 could be joined in series to a 24 V power source 47. The batteries could be replaced with any other power source that generates 24 volts and may include such devices as solar cells, wind generators, AC to DC transformers, etc. Suitable safety features could include a ground fault interrupt (GFI), fuses, etc. This list should not be considered all inclusive but merely a representation of possible alternatives. The 24V power supply 47 would be attached to the PLC 50. The PLC 50 would then electrically connected by wiring with the linear solenoids 18 so that the voltage on an output pin of PLC 50 would actuate all of the solenoids at once.

Another input to the PLC 50 could be a push button or switch 58 for starting the dispensing process. When the switch has been activated, the PLC 50 would maintain the output voltage a predetermined amount of time to cause actuators 18 to depress press bars 34 in a controlled manner and for a certain time to cause the pump-action misting heads 26 to issue a gentle burst or cloud of misted artificial tanning solution. Once the certain programmed amount of time has passed, the PLC 50 would discontinue the application of a voltage. Solenoids 18 would retract with the removal of the power supply and the pump-action emitters 26 would return to their home or normal position through the use of a spring built within the misting heads 26.

Additional outputs from the PLC 50 could be used to provide visual and audio cues to the client to facilitate recumbent artificial tanning. An output of the PLC 50 could be to a simple light 53 that lights up right before the dispensing of artificial tanning solution. The same (or another) output of the PLC 50 could be used to provide an output that would energize a simple buzzer 52 that would emit a sound before the dispensing of artificial tanning solution.

Other more elaborate visual and audio cues and instructions to the client could be provided by programming and/or use of a more elaborate PLC or microprocessor to provide outputs that would trigger audio and visual recordings. These further instructions could be provided through the use of a display screen 54 (e.g. Liquid Crystal Display (LCD)) and/or an audio player (e.g. MP3 player). These additional means of communicating instructions should be considered examples of possible embodiments.

Figure 8:
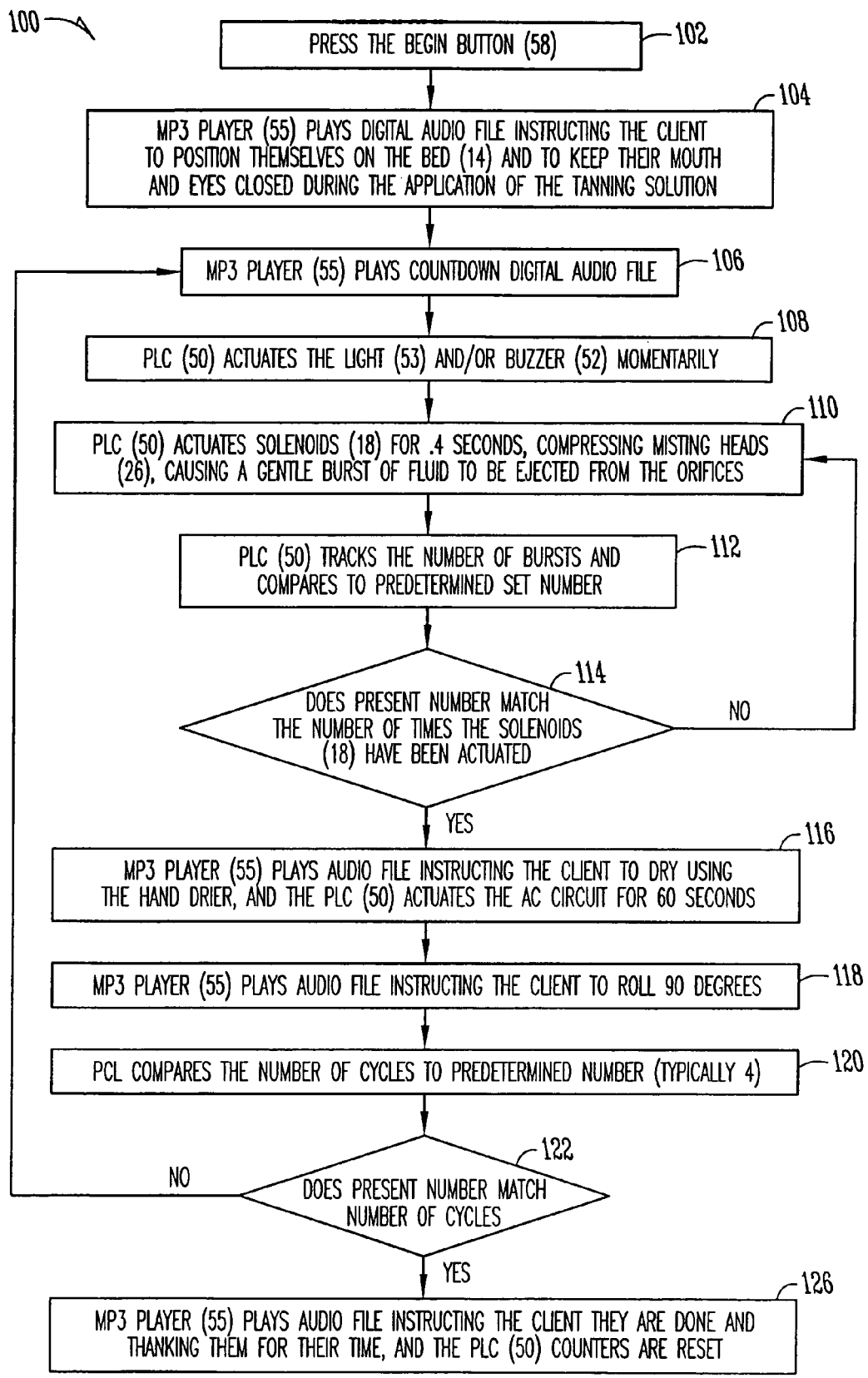
FIG. 8 is a flow chart of one regimen of operation of any of the exemplary embodiments according to the programmable control system of FIG. 4.

An example of a programmed regimen for system 10 is illustrated in the flow chart 100 of FIG. 8. A client or user would hit a "begin" button to start an artificial tanning treatment. There could be a "system on/off" or "power up" button or switch 60. PLC 50 would monitor if a client or user has pressed a "begin" button (step 102). If so, PLC 50 would instruct operation of MP3 player 55 to play a digital audio file to announce audibly to the user what to do first (e.g. "Please lay on your back on the table") (step 104). PLC would then instruct MP3 player 55 to play a "count-down" audio file (e.g. "Bursts of spray will commence in ten seconds; ten, nine, eight, seven, six, five, four, three, two, one") (step 106). After the countdown, PLC 50 could momentarily turn on light 53 and/or buzzer 52 to alert the user that spraying will commence (step 108).

The client would lay upon the bed 14 positioned such that coverage from the tanning solution emitted from the misting heads 26 would cover the client from the crown of the head to the bottom of the client's feet. The MP3 player could optionally play (not shown) an audio file reminding the client to close his/her mouth during the bursts and to not inhale. The client would initially lie upon their backs on the bed 14 with limbs extended straight so as to prevent excessive creasing of the skin or overlapping of limbs.

PLC 50 would issue an instruction to solenoids 18 and cause them to press misting heads to issue a first controlled, gentle burst of misted solution (step 110). PLC 50 would apply a voltage to the actuators 18 and actuate the solenoids 18 such that the all of the solenoids' rods 44 would extend pressure downward on the press bar 34. The pressure on the press bar 34 would then be transferred to the upper surface of the pump action emitters 26 causing them to eject the artificial tanning solution into a fine mist. This fine mist would then fall and evenly dissipate over the client. The dissipation would create a fine and even coating of the client.

PLC 50 would then instruct seven more successive bursts (there can be a short pause in-between) (steps 110-114). The user would thus get eight bursts while lying on his/her back). As discussed, system 10 creates a very fine mist through bursts that almost evaporate on contact with the body.

PLC 50 would then instruct the customer, via an audio file, to stay in place for one minute and/or operate a forced air dryer for approximately one minute (step 116). As illustrated in FIG. 1, it could be a conventional commercially available hand-held hair dryer 64. For example, the client could use a hand operated dryer 64 that provides a high flow of 95° F. air to dry the client's skin between applications of the tanning solution. The hand dryer 64 could be plugged into an electrical outlet separate to the circuit described in FIG. 4. Alternatively, and preferably, there could be a larger automatically controlled air dryer mounted on frame 16 with air outlets directed towards bed 14. Once a set of bursts is completed, PLC 50 could instruct the MP3 player to instruct the user to turn or roll ninety degrees to prepare for application on another side (step 118). The automated drying could use any type of mechanism to provide drying action to the user. The example would be two hand held dryers like dryer 64 of FIG. 1, mounted on opposite sides of frame 16 and pointed toward the user. At the appropriate time, the apparatus could automatically start them and run them for a given period. Alternatively, there could be a blower like reference 36 of FIG. 3 which supplies pressurized air to conduit 38 to distribute the drying air out orifices 40. Another example is a whisper fan with heating element that could direct heated air on the user. Other alternatives are possible.

PLC could be programmed to go through three additional loops of steps 106-122. At step 118, an audio file could be played instructing the client to turn to a next side (e.g. "Please turn and lay on your right side"). The client then rotates 90° so that the client is then laying on his/her side on the bed 14. Again system 10 announces a count down (step 106), the PLC 50 then actuates the solenoids 18 for eight bursts (steps 110-114), and a fine mist is created that covers that side of the client's body. Again the client uses the hand dryer 60 to assist in the drying process (step 116). Another audio file is played (e.g. "Please turn and lay on your stomach") (step 118), followed by a countdown, eight bursts, and a minute drying time (steps 106-116). The client then rolls another 90° so that the client is now laying upon his/her stomach. The solenoids 18 actuate and the client's backside is covered with a fine mist of artificial tanning solution. Finally, an audio file is played (e.g. "Please turn and lay on your left side"), and eight bursts and a minute drying time are given. The client rolls a final 90° and the client is coated a final time with tanning solution.

The client is finished after the final drying period. Once the PLC has gone through the four loops to coat the four sides of the client (steps 120, 122), the program moves out of the loop. An audio file could instruct the client (e.g. "Your treatment is now done. Please move off the table. Thank you for your business.") (step 126). The program then returns to monitor for the next push of the begin button (step 102).

As can be seen by the foregoing description of system 10, it meets the objects, features, advantages, and aspects of the invention. It provides a non-complex apparatus and method of promoting semi-automatic or automatic application of artificial tanning solution, in a non-complex, safer form. It deters inhalation or application to non-approved areas of the body. In deters over application or drips. It promotes an even application and deters need for post-application work (e.g. rubbing or toweling). It can be performed with an economical amount of artificial coloring dispensed (for example, around or under 100 ml fluid ounces per treatment or on the order of 50 treatments per gallon of solution). It does not require enclosure, containment, and capture of the coloring. It can be implemented in a relatively small (e.g. 7 feet by 4 feet-can fit in vans, and perhaps mini-vans and SUVs), lightweight (e.g. 20 to 50 pounds), and even portable apparatus that could be powered by battery.

E. Specific Exemplary Embodiment Two

Another embodiment of an artificial tanning system is one in which the client remains upright while having the tanning solution applied. FIG. 3 depicts an upright artificial tanning system 12. It incorporates many similar features of the recumbent system 10 of FIG. 10. It has a 2×4 wood frame 16. It has a reservoir 22 which feeds artificial tanning solution to a plurality of misting heads 26 by gravity. It has solenoid actuators 18 that operate press bars 34 to create controlled gentle bursts from misting heads 26.

However, instead of having a single row of misting heads 26, the upright system has multiple rows. The multiple rows are positioned vertically on several sets of metal plates 28/30 via the use of ⅜" threaded steel rods 32 and nuts 33. Just as in the recumbent tanning system 10, the misting heads 26 are mounted on the lower mounting plate 30 and the feed tubes 42 attach to a vinyl tube 24 used to carry artificial tanning solution. The solenoids 18 for each push bar 34 are mounted on the upper mounting plate 28 just as in the recumbent artificial tanning system 10.

Upright tanning system 12 has a hot air blower 36 connected to PVC pipe 38. The PVC pipe 38 has ⅛" diameter holes 40 positioned such that the resulting airflow is parallel and in the same direction as the fluid misted from the pump action misting heads 26. The airflow assists in the even application of artificial tanning solution to the client's body. The air flow can also be used between applications of the artificial tanning solution to facilitate drying the client's body. The PLC 50 would control the activation and deactivation of the hot air blower 36.

The method of use of the upright artificial tanning system 12 would be similar to the recumbent artificial tanning system 10. The client would be coated with artificial tanning solution four times for each side of his/her body. Between applications the client would use warm air to more rapidly dry their skin. The upright system 12 could also provide audio and visual cues to the client to facilitate proper use of the artificial tanning system.

This exemplary embodiment is adapted to treat a person in an upright position with the same or similar aspects, advantages, features, or objects as the first specific embodiment. This upright embodiment has a very thin profile and would not take up much floor space.

F. Options and Alternatives

It will be appreciated that the foregoing exemplary embodiments are for example only, and not by way of limitation of the invention. Variations obvious to those skilled in the art will be included within the scope of the invention. The precise materials, connections, and configurations shown and described with respect to the exemplary embodiment can vary.

With respect to the recumbent tanning system 10 of FIG. 1, the bed 14 could be built with legs supporting the bed's surface. Bed frame 15 could also be constructed with table legs or box frame such that it is collapsible facilitating the portable nature of the invention. Another means of supporting the bed's surface would be with a hinge mounted on the bottom portion of the frame 16 and attached to the bed 14 so that the bed could be folded up or down when not in use. Bed frame 15 could be constructed of alternative materials including: wood, metal, poly vinyl chloride (PVC) pipe, and plastic. There could be wheels or other structure or components to assist in moving the apparatus.

Figure 7:
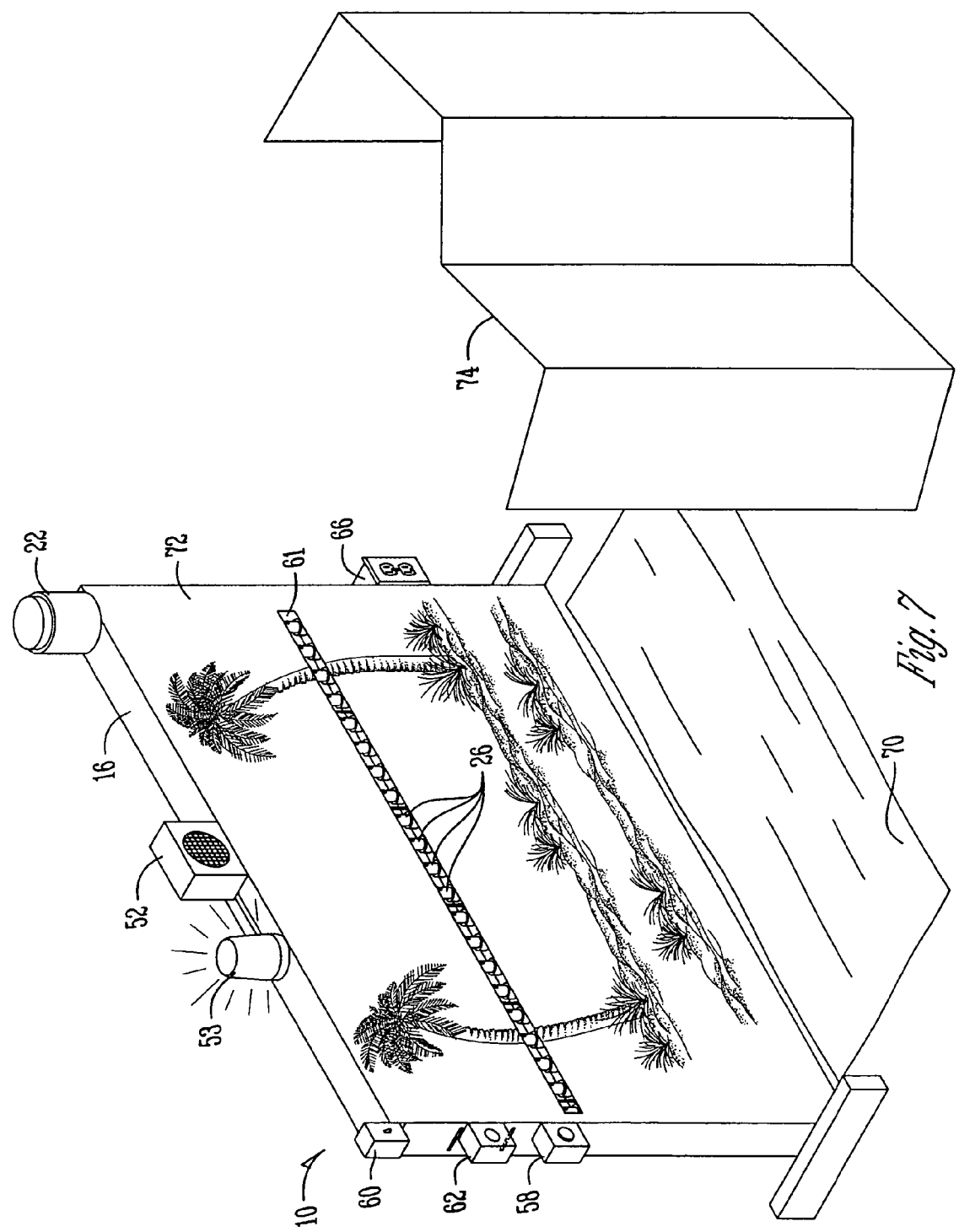
FIG. 7 is a perspective view of a recumbent system with an optional front screen, according to another exemplary embodiment of the present invention.

The mattress pad 13 of the bed can also be varied to achieve different purposes. The mattress pad 13 is intended to provide the client with a comfortable surface to recline upon. The mattress pad 13 could be constructed with materials that is chemically and stain resistant. The mattress pad 13 could also incorporate a material with a rubberized surface so as to prevent accidents caused by a slippery, wet surface. Another means of addressing the minimal amount of tanning solution overspray would be to cover the surface of bed 14 with a disposable absorbent mat. A disposable absorbent mat 70 could also be utilized in the upright artificial tanning system as depicted in FIG. 7.

There are other options and/or features that can be implemented on multiple embodiments. For example, a closed fluid circuit could be used in either an upright 12 or recumbent 10 artificial tanning systems. The closed fluid circuit would include a reservoir 22, vinyl tubing 24, and a submersible pump (not shown) to circulate artificial tanning fluid through the circuit. The submersible pump could be, but is not limited to, a Little Giant Pump Company PE-1 catalog number 518200. The preferred pump would have a maximum lift of 7' and would have a ¼" MNPT discharge. The discharge should be 3.0 PSI with a volume of 170 GPH at a 1' lift. The intake should be screened and could have a 6' outlet cord. Other pumps with similar specifications could be utilized. A DC powered submersible pump could be used to circulate the artificial tanning solution through the fluid circuit.

Another alternative to the fluid circuit would be to alternate the number of misting heads 26. The detailed examples depict an artificial tanning system with twenty misting heads 26 each. The number of misting heads 26 could be varied to achieve needed and desired effects. These needs could include altering the length of the bed 14 to facilitate taller clients or to fit the artificial tanning system to the specific dimensions of a room. The number of misting heads 26 could also be varied to facilitate using different misting heads 26 with different emitting patterns and volumes.

Another means of insuring that the client receives a uniform application of artificial tanning solution is to provide a one fluid ounce spray bottle 68 of artificial tanning solution to the client. The client would then be able to make small modifications to their artificial tan as necessary or desired post-treatment at home. The client would simply apply a small amount of artificial tanning solution to the desired area and allow it to dry to correct any small imperfection in the client's artificial tan.

The electrical system is another feature that can be modified on multiple embodiments. To increase the safety of the clients and operators of the artificial tanning system a simple emergency machine off (EMO) 62 switch could be included. Ground Fault Interrupter (GFI) outlets 66 could also be used in the electrical system to reduce the possibility of anyone being shocked while using the artificial tanning system.

The instructions provided to the client could also be delivered through other means. A written set of instructions could be posted on or near the artificial tanning system. The instructions could also be delivered through automated audio and visual instructions. Instead of using an MP3 player 55 a DVD or DVR system could provided the audio instructions. At the same time the same devices could provide visual instruction to the client as they operate the artificial tanning system. Another method of controlling the operation of the artificial tanning system would be a computer and monitor with the correct hardware and software to operate the solenoids and other devices. The computer monitor and attached speakers could also provide the visual cues described above.

Figure 5:
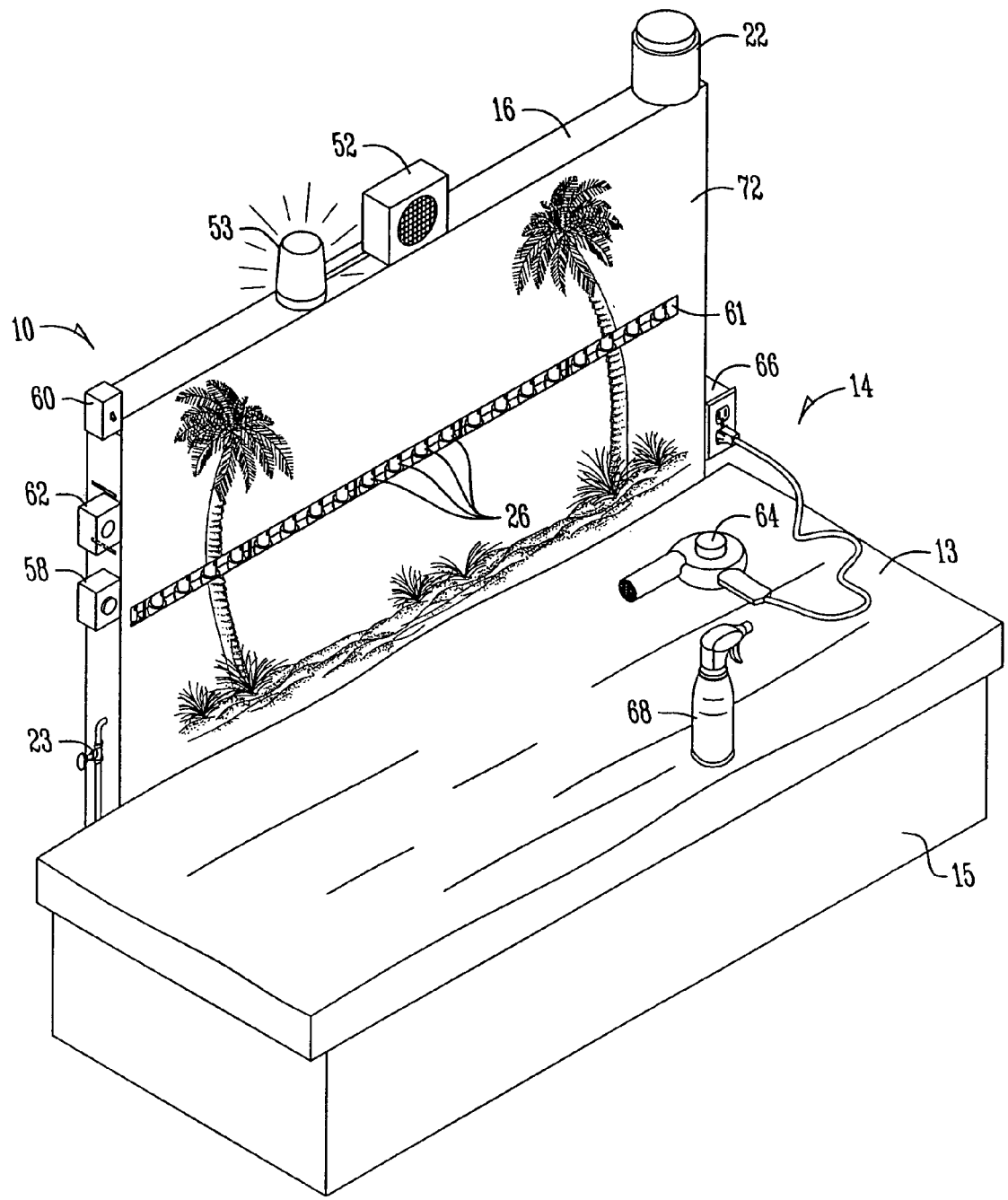
FIG. 5 is a perspective view of a recumbent artificial tanning system with a background screen according to another exemplary embodiment of the present invention.
Figure 6:
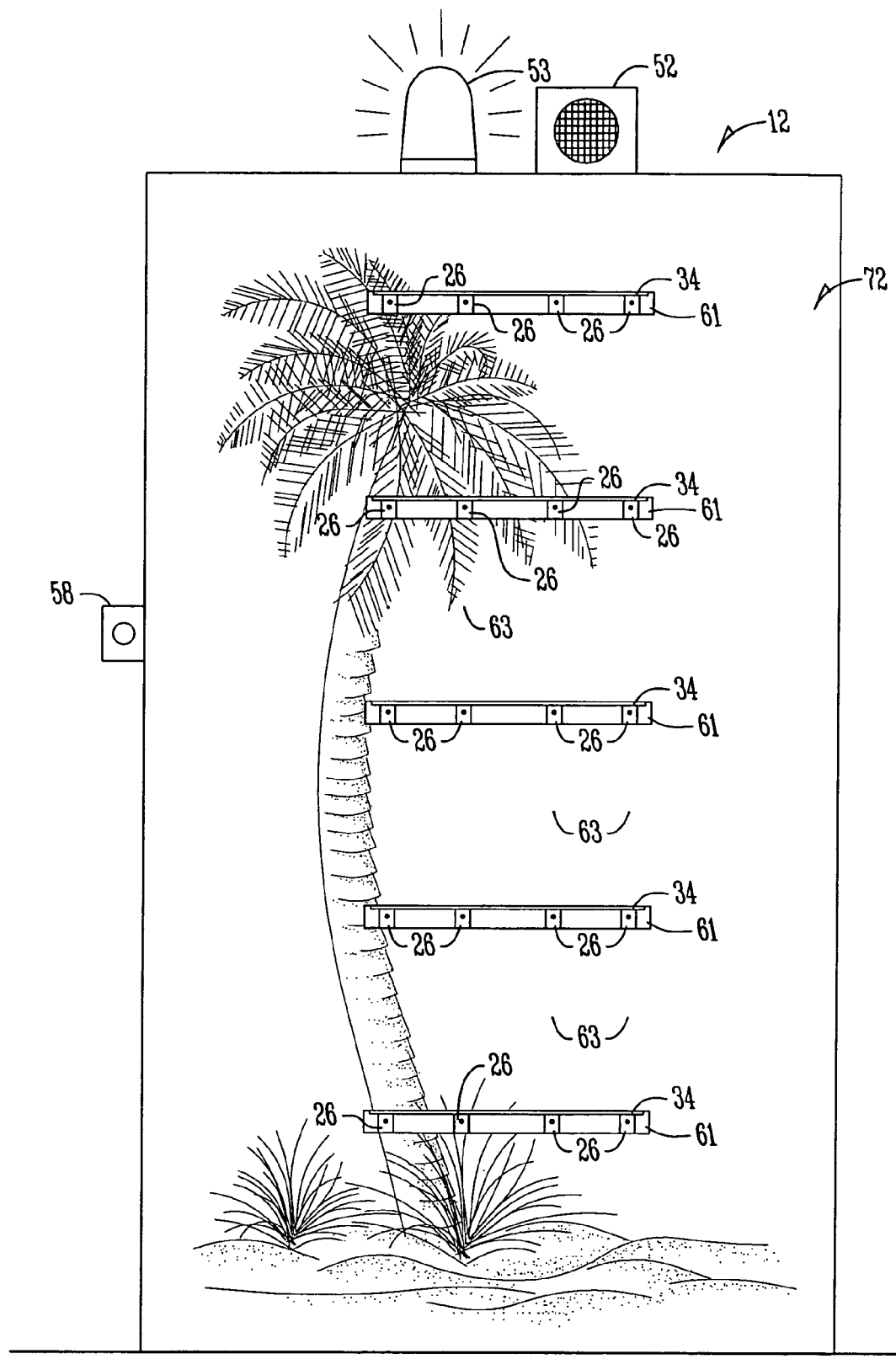
FIG. 6 is a front elevation view of an upright artificial tanning system with a background screen according to another exemplary embodiment of the present invention.

The appearance of the artificial tanning system can be varied through the inclusion of a decorative screen 72 (see, e.g., FIGS. 5-7). The decorative screen would cover the misting head frame 16 with openings in front of the misting heads 26. It could be fabric or sheet material and tacked, adhered or otherwise mounted on frame 16. The decorative screen 72 could have any number of designs, logos, words, and or pictures printed upon it. For example, it could include aesthetically pleasing images (e.g. to simulate a beach or tropical environment). It could include other graphics or text (e.g. advertising or instructions). It would not add significantly to the size or weight of the system. The owner of the artificial tanning system 10 could even sell advertising space utilizing the decorative screen 72. Drying air jets could issue through opening(s) 61 and/or openings 63 in the screen 72.

The appearance of the artificial tanning system could also be modified through the inclusion of a privacy screen 74 as depicted in FIG. 7. An upright artificial tanning system 12 could also have a privacy screen 74. This screen could be modified to include the same appearance as the decorative screen 72 and could also be used to advertise products and services. The privacy screen 74 would not necessarily be necessary if the artificial tanning system 10 or 12 was installed in a dedicated room. Privacy screen 74 could be an approximately 7 feet tall and four foot wide accordion type privacy dressing screen (e.g. fabric or paper on wood, wire, or plastic frame). This would provide substantial privacy to the user but it is light weight, folds up and is portable, and does not require complete enclosure.

To facilitate ease of maintenance, the upright or recumbent artificial tanning systems 12 or 10 could be constructed in a modular manner. Examples include, but are not limited to, the misting head subsystem, the solenoid subsystem, the PLC. This enables any repairs to be completed without having to trouble shoot the individual defective device. An example would be to replace the entire misting head assembly 25 with another misting head assembly 25, instead of trying to determine why a single actuator 18 is not responding. The owner/operator of the artificial tanning system would simply have to replace the module and allow the manufacturer to troubleshoot the defective module at a more leisurely pace. This can be advantageous in that a whole subsystem can be manufactured (for efficiency in manufacturing). If a business is relying on a system 10 or 212 for substantial income and customer satisfaction, and the system needed repair or maintenance, instead of waiting for a trained technician to evaluate and repair the system, a whole subsystem could be sent by overnight carrier and the proprietor or someone with less skill than a trained technician many times could get the system running again without substantial delay.

While the exemplary embodiments have discussed application of artificial tanning solutions, the system may work with other fluids. Examples might be insect repellants, cosmetic applications, medical applications, sunscreen, and hydrosols for aroma therapy or for any other application where the applicant wants to decrease the probability of ingesting the applied liquid.

Instead of one or more solenoids moving a press bar against several spray heads, individual solenoids (smaller than those described in FIG. 1) could directly press individual spray heads. Each solenoid/spray head pair could be made as a modular unit. Thus, if one solenoid or spray head malfunctioned or broke, that unit could be replaced, instead of replacing a set of solenoids, press bar, and spray heads.

A general description of the present invention, as well as preferred embodiments of the present invention, has been set forth above. Those skilled in the art to which the present invention pertains will recognize and be able to practice additional variations in the methods and systems described which fall within the teaching of this invention. Accordingly, all such modifications and additions are deemed to be within the scope of the invention which is to be limited only by the claims appended hereto.

What is claimed is:

1. An apparatus for applying an artificial tanning solution to a person's skin comprising:
   a. a framework at or near a substantially non-enclosed application space above a bed surface having a length and width and which can support a prone human body;
   b. a plurality of misting heads mounted on a support member of the framework in a row at spaced apart positions above and along the length of the bed surface, the misting heads each having a top and a bottom and comprising a spray pump assembly comprising an inlet, an outlet orifice, and a piston valve moveable over a range of travel in a compression chamber between first and second positions to pump fluid between the inlet and outlet orifice, the outlet orifice having a dispensing direction generally normal to the plane along the framework;
   c. a conduit in fluid communication between the misting heads and a reservoir;
   d. an actuator having a controllable input and output, the output operatively connected to the plurality of misting heads via a linkage interfaced with each misting head, the linkage comprising one or more elongated press bars spanning the tops of the misting heads and one or more arms extending to the actuator and moveable by the output of the actuator over the range of travel to move the piston valve of the misting heads between first and second positions; and
   e. a control component operatively connected to and actuating the actuator, the control component controlling stroke, force, and speed of movement of the piston valves of the misting heads to cause coordinated, controlled in time and quantity gentle bursts of said fluid in misted form to move out from the outlet orifices of the plurality of misting heads above the bed surface into the application space, expand, and then fall by gravity by coordination of each of the plurality of misting heads in force and amount of movement down to and along the bed surface.

2. The apparatus of claim 1 wherein the apparatus is without any substantial enclosure to contain the bursts.

3. The apparatus of claim 1 wherein there is no capture structure or component to capture fluid for reuse.

4. The apparatus of claim 1 wherein the framework is sized to support the plurality of misting heads in an array spaced apart to correspond to the application space and bed surface.

5. The apparatus of claim 4 wherein the application space and bed surface correspond to a human body.

6. The apparatus of claim 5 wherein the application space and bed surface correspond to a prone human body.

7. The apparatus of claim 4 wherein the array comprises a single row of misting heads.

8. The apparatus of claim 7 wherein the array comprises a plurality of rows of misting heads.

9. The apparatus of claim 1 wherein the misting heads issue fluid at relatively low pressure.

10. The apparatus of claim 1 wherein a burst is approximately for $2/3^{rd}$ second at relatively low psi.

11. The apparatus of claim 1 wherein the misting heads are manual push spray heads with resilient return to normal position.

12. The apparatus of claim 11 wherein the actuator comprises one or more devices to convert electrical power to mechanical force sufficient to operate the manual push sprays heads.

13. The apparatus of claim 12 wherein the actuator comprises one or more electrical solenoids.

14. The apparatus of claim 1 wherein the fluid is an artificial tanning solution.

15. The apparatus of claim 14 wherein the artificial tanning solution is DHA at approximately 8.5% in water.

16. An apparatus for application of a fluid to a person or animal comprising:
   a. a framework;
   b. a plurality of misting heads mounted on the framework, the misting heads comprising manual push type spray heads with resilient return to normal position;
   c. a conduit in fluid communication between the misting heads and a reservoir of said fluid;
   d. an actuator operatively connected to the misting heads adapted to cause a controlled in time and quantity gentle burst of said fluid in misted form to move out from the misting heads and then fall by gravity without any substantial enclosure to contain the burst; the actuator comprising a electrically powered component adapted to move a member to depress the spray heads and release the spray heads to return to normal position;
   e. an application area under or adjacent the misting heads;
   f. a control circuit operatively connected to the actuator.

17. The apparatus of claim 16 wherein the reservoir is positioned to supply fluid to the spray heads by gravity.

18. The apparatus of claim 16 further comprising a pump to move the fluid from the reservoir to the spray heads.

19. The apparatus of claim 16 wherein the application area comprises a volume of space above a floor area where a user stands.

20. The apparatus of claim 16 wherein the application area comprises a volume of space where a user lies generally horizontally.

21. The apparatus of claim 20 further comprising a bed defining the application area.

* * * * *